United States Patent
Perez Barraza et al.

(10) Patent No.: US 12,392,744 B2
(45) Date of Patent: Aug. 19, 2025

(54) SENSOR FOR MEASURING A GAS PROPERTY

(71) Applicant: Infineon Technologies AG, Neubiberg (DE)

(72) Inventors: Julia Isabel Perez Barraza, Unterhaching (DE); Matthias Eberl, Taufkirchen (DE); Francesco Solazzi, Villach (AT)

(73) Assignee: Infineon Technologies AG, Neubiberg (DE)

( * ) Notice: Subject to any disclaimer, the term of this patent is extended or adjusted under 35 U.S.C. 154(b) by 810 days.

(21) Appl. No.: 17/457,752

(22) Filed: Dec. 6, 2021

(65) Prior Publication Data

US 2022/0196585 A1  Jun. 23, 2022

(30) Foreign Application Priority Data

Dec. 21, 2020 (DE) .......................... 102020134366.3

(51) Int. Cl.
  *G01N 27/12* (2006.01)
  *G01N 33/00* (2006.01)

(52) U.S. Cl.
  CPC ......... *G01N 27/122* (2013.01); *G01N 27/129* (2013.01); *G01N 33/005* (2013.01); *H01L 2924/0002* (2013.01)

(58) Field of Classification Search
  None
  See application file for complete search history.

(56) References Cited

U.S. PATENT DOCUMENTS

| | | | | |
|---|---|---|---|---|
| 4,525,704 A | * | 6/1985 | Campbell | C12Q 1/46 435/817 |
| 5,656,827 A | * | 8/1997 | Kang | G01N 27/129 257/253 |
| 5,786,744 A | * | 7/1998 | Nishio | G01P 15/08 338/14 |
| 5,831,146 A | * | 11/1998 | Newman | G01N 33/0047 73/23.31 |
| 9,746,437 B1 | * | 8/2017 | Chiou | H10D 84/0135 |

(Continued)

FOREIGN PATENT DOCUMENTS

DE  2714040 A1  10/1978
DE  69531031 T2  3/1996
(Continued)

OTHER PUBLICATIONS

Hashmi et al., "Comprehensive Materials Processing: Review of Recent Developments in Sensing Materials, 13.03.2.2 Platinum", Elsevier, 2014, pp. 61, ISBN: 978-0-08-096533-8 (Year: 2014).*

*Primary Examiner* — Neil N Turk
*Assistant Examiner* — Benjamin Joseph Kass
(74) *Attorney, Agent, or Firm* — Harrity & Harrity, LLP (57) ABSTRACT

It is proposed a sensor for measuring a gas property, wherein the sensor comprises a semiconductor die, wherein the semiconductor die comprises a reference cavity and a measuring cavity, wherein a reference sensor element is arranged in the reference cavity, wherein a measuring sensor element is arranged in the measuring cavity, wherein the reference cavity is sealed from ambient gas, wherein the measuring cavity is fluidly connected to ambient gas. Further it is proposed a method for manufacturing such a sensor.

22 Claims, 9 Drawing Sheets

(56) References Cited

U.S. PATENT DOCUMENTS

| | | | | |
|---|---|---|---|---|
| 2003/0039299 | A1* | 2/2003 | Horovitz | G01N 27/16 |
| | | | | 374/31 |
| 2008/0059041 | A1* | 3/2008 | Kida | F02D 41/1443 |
| | | | | 701/101 |
| 2015/0014167 | A1* | 1/2015 | Dziallas | G01N 27/4074 |
| | | | | 204/415 |
| 2015/0101395 | A1* | 4/2015 | Dehe | G01N 29/30 |
| | | | | 73/24.02 |
| 2016/0153947 | A1* | 6/2016 | Kullik | A61M 16/12 |
| | | | | 73/31.05 |
| 2018/0238822 | A1* | 8/2018 | Chen | G01N 27/122 |
| 2019/0376919 | A1* | 12/2019 | Hattori | G01N 27/16 |
| 2020/0080951 | A1* | 3/2020 | Nakano | G01N 27/18 |

FOREIGN PATENT DOCUMENTS

| | | |
|---|---|---|
| DE | 10121610 A1 | 11/2002 |
| DE | 102004033597 A1 | 2/2006 |
| DE | 102017215527 A1 | 3/2019 |
| DE | 102018207689 A1 | 11/2019 |
| DE | 102019216129 A1 | 4/2021 |
| WO | 2009095494 A1 | 8/2009 |

* cited by examiner

SENSOR FOR MEASURING A GAS PROPERTY

CROSS REFERENCE TO RELATED APPLICATION

This application claims priority to German Patent Application No. 102020134366.3, filed on Dec. 21, 2020, the contents of which are incorporated by reference herein in their entirety.

TECHNICAL FIELD

The disclosure relates to a sensor for measuring a gas property and a method for manufacturing a sensor for measuring a gas property.

BACKGROUND

There is an increasing demand for reducing the consumption of petroleum and shifting to using green energy. For example, hydrogen generated by wind turbines is considered as a possible green fuel for automotive applications.

Sensors may be required to detect any leaking hydrogen to avoid the formation of Oxyhydrogen.

A highly sensitive hydrogen sensor to be operated at room temperature is disclosed in DE 10 2004 033597 A1. However, cars may be operated at temperatures well below and above room temperature.

SUMMARY

Implementations described herein relate to a sensor for measuring a gas property being more suitable for automotive applications.

Subject-matter as defined in the independent claims is provided. Further implementations are described in the dependent claims.

There is proposed a sensor for measuring a gas property. In some implementations, the sensor may measure a gas composition. In some implementations, the sensor may measure a hydrogen level. The sensor comprises a semiconductor die, wherein the semiconductor die comprises a reference cavity and a measuring cavity. A reference sensor element is arranged in the reference cavity and a measuring sensor element is arranged in the measuring cavity. The reference cavity is sealed from ambient gas and the measuring cavity is fluidly connected to ambient gas. A fluid connection may relate to a connection allowing the passing of liquids and/or gas. For example, the reference cavity may be covered with a membrane allowing diffusion of gas into the reference cavity.

Implementations described herein may relate to a method for manufacturing one or more sensors for measuring a gas property, a gas composition, and/or a hydrogen level. The method comprises providing a semiconductor wafer having a front side and a backside. A well with a doping type opposite of the doping type of the semiconductor wafer is provided at the front side of the semiconductor wafer. Conductive regions within or at the surface of the membranes are provided. In some implementations, the conductive regions may be provided by doping and/or by depositing a conductive material. At least one reference sensor element and at least one measuring sensor element are formed from the conductive regions by etching. At least one covering wafer is bonded to the semiconductor wafer for sealing the reference cavity and covering the measuring cavity.

BRIEF DESCRIPTION OF THE DRAWINGS

Implementations of the proposed sensor and the proposed method for manufacturing a sensor will now be explained with reference to the drawing. In the drawing

DETAILED DESCRIPTION

Figure 1:
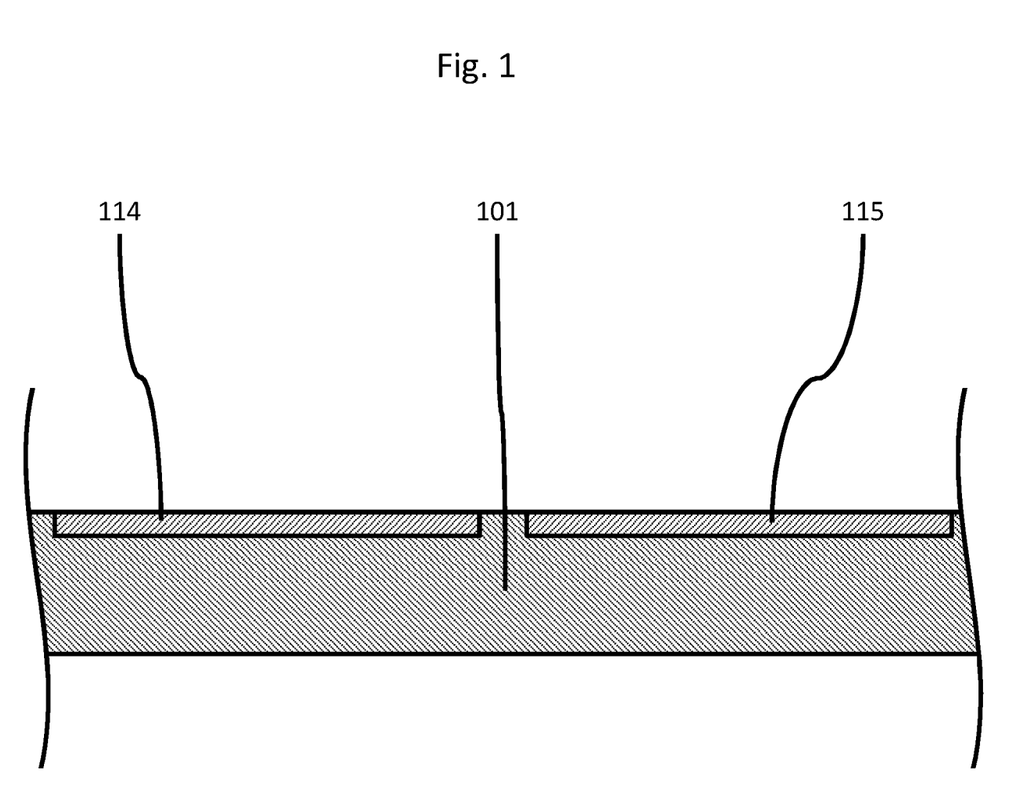
FIG. 1 shows a wafer.

FIG. 1 shows semiconductor wafer 101 with doped wells 114 and 115. The doped wells 114 and 115 have a doping type opposite to the doping type of the semiconductor wafer 101. The wells 114 and 115 are provided at the front side of the semiconductor wafer 101.

Figure 2:
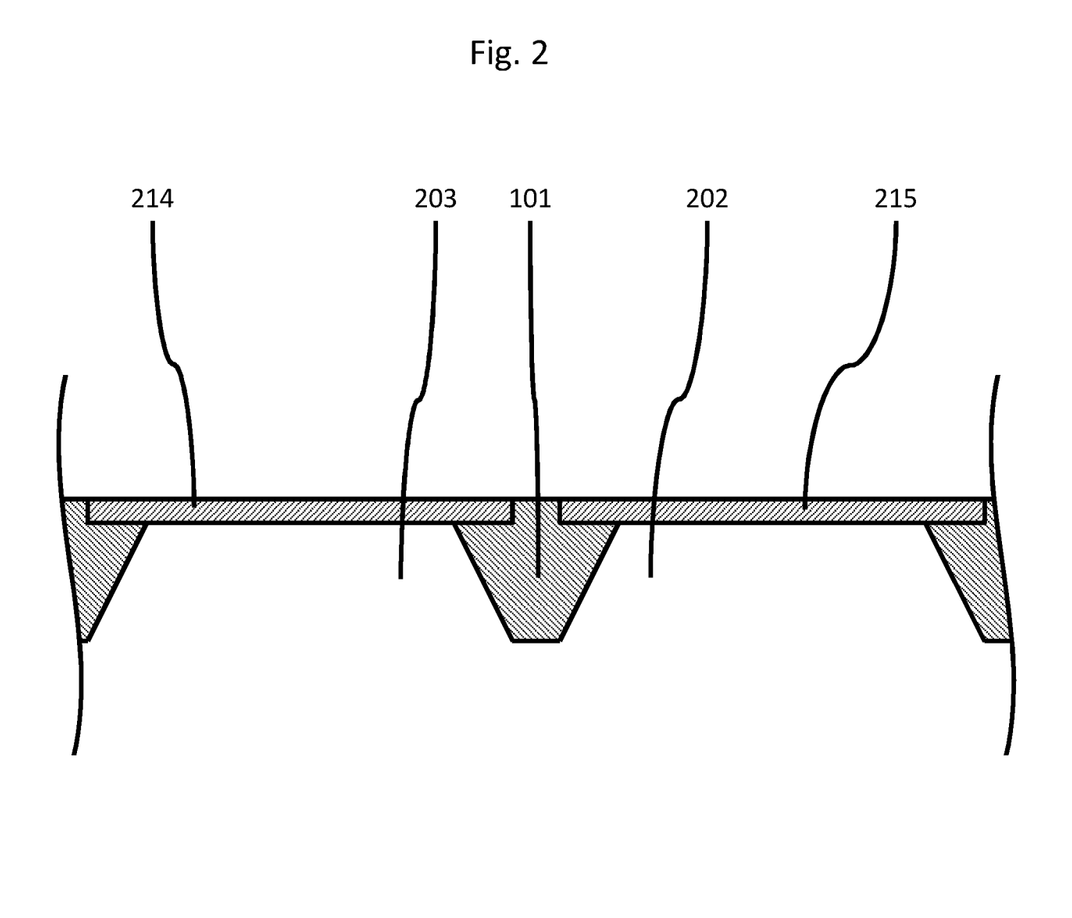
FIG. 2 shows the processed wafer of FIG. 1.

As shown in FIG. 2, at least one reference cavity 202 and at least one measuring cavity 203 are etched in the backside of the semiconductor wafer 101 to form membranes 214 and 215.

The large back side cavities 202 and 203 may be formed using a pn-etch. The wells 114 and 115 may be n-doped and the semiconductor wafer may be a p-doped silicon wafer.

Figure 3:
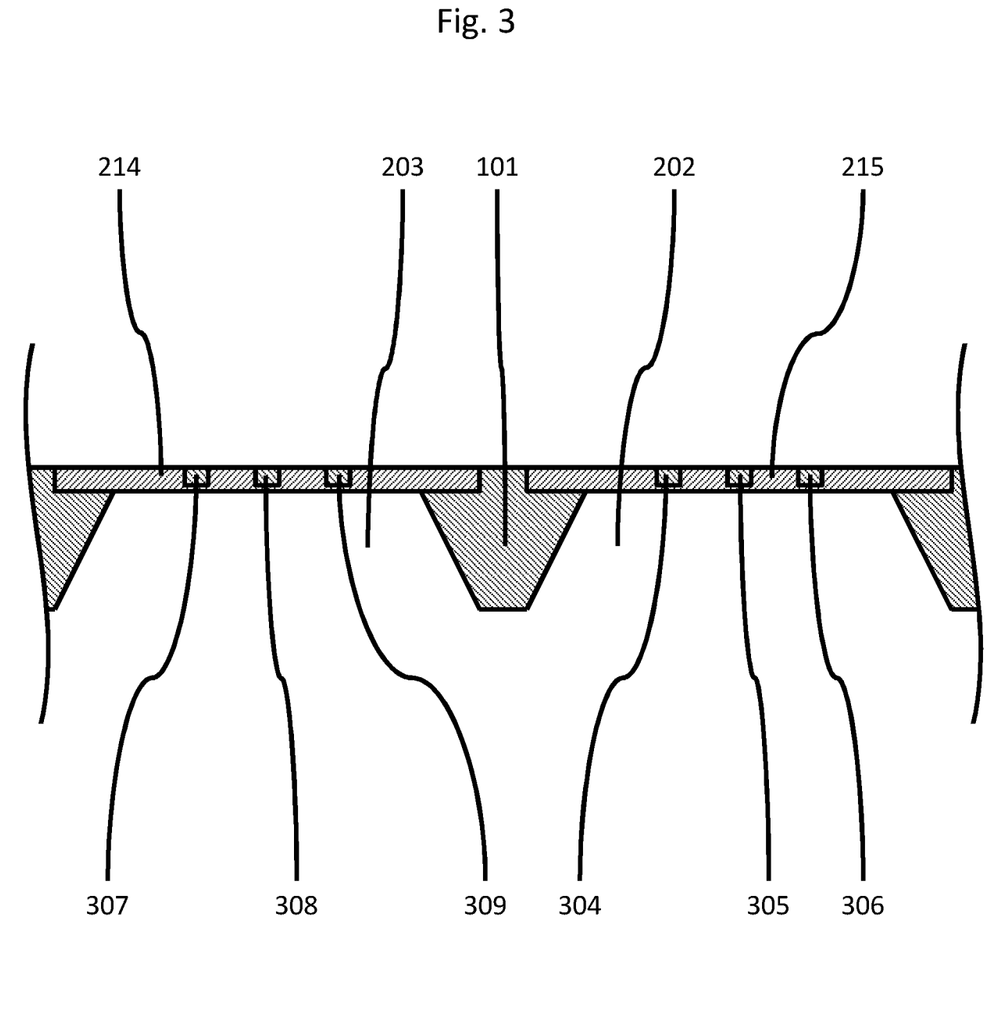
FIG. 3 shows the processed wafer of FIG. 2.

FIG. 3 shows the wafer 101 after conductive regions 304, 305, 306, 307, 308, and 309 have been formed within the surface of the membranes 214 and 215. The conductive regions 304, 305, 306, 307, 308 and 309 may be formed by doping. Alternatively or in addition, the conductive regions 304, 305, 306, 307, 308, and 309 may be formed by depositing a conductive material.

Figure 4:
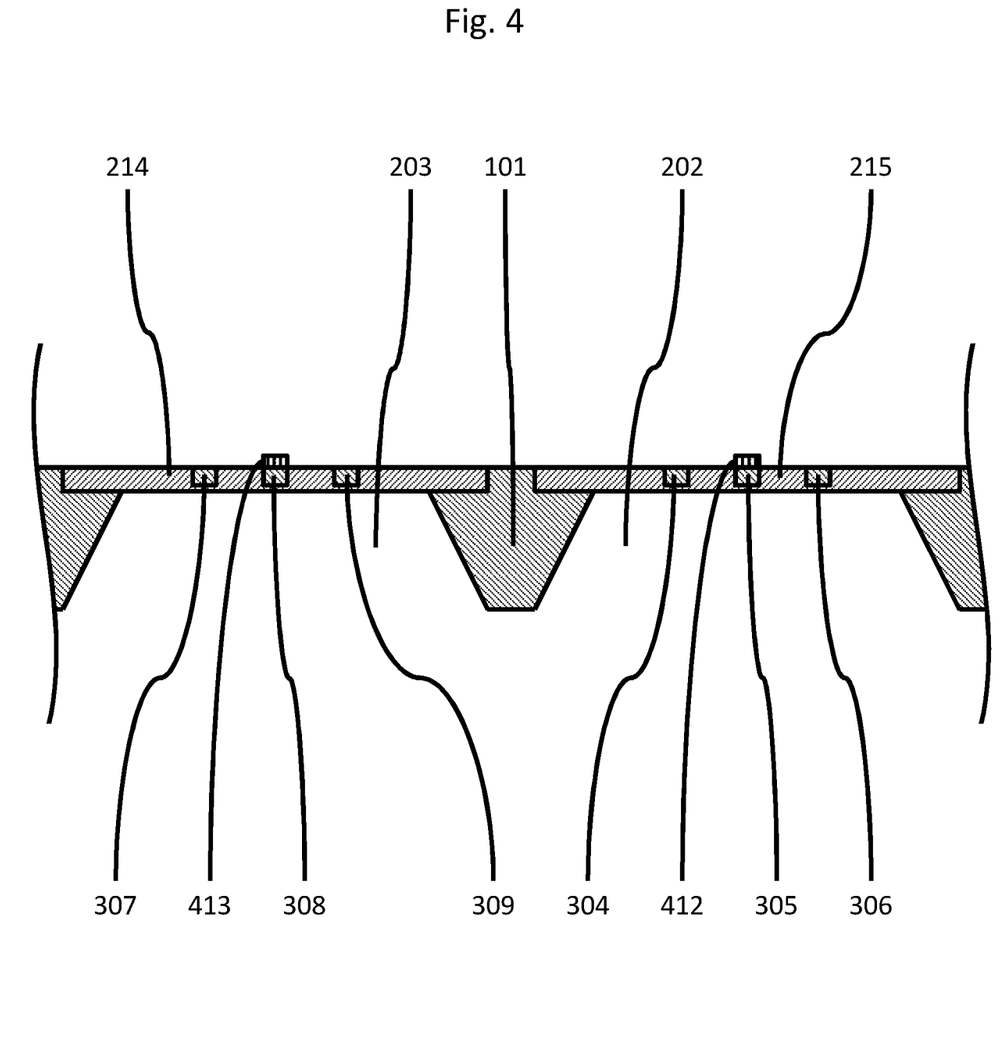
FIG. 4 shows the processed wafer of FIG. 3.
Figure 5:
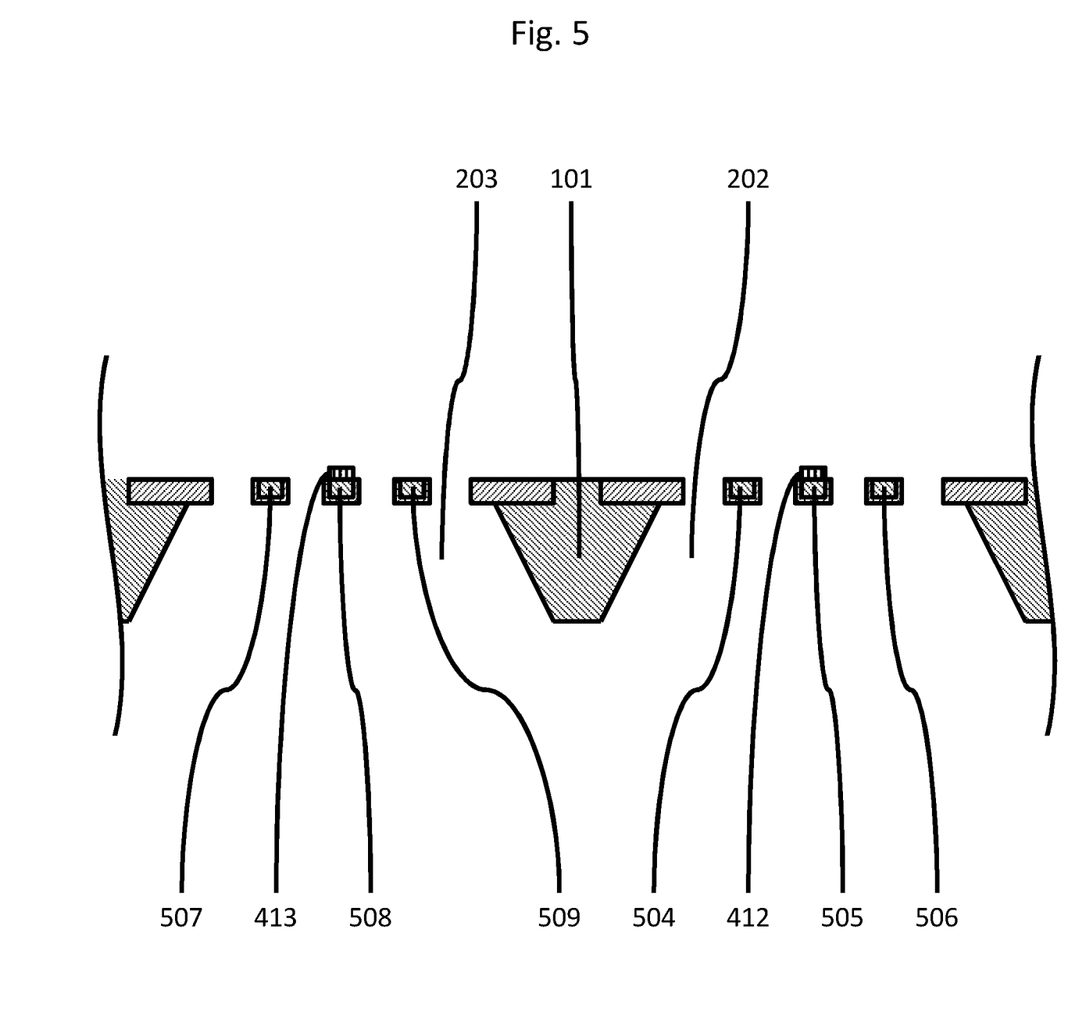
FIG. 5 shows the processed wafer of FIG. 4.

As shown in FIG. 4, a catalytic layer 412 may be formed on the conductive region 305 and a further catalytic layer 413 may be formed on the conductive region 308. The catalytic layers 412 and 413 may be configured for reacting with gas molecules. In some implementations, the catalytic layer may be formed from a noble metal. For example, platinum and/or palladium may be deposited for reacting with hydrogen molecules. Three reference sensor elements 504, 505 and 506 as well as three measuring sensor elements 507, 508 and 509 may be formed from the conductive regions 304, 305, 306, 307, 308 and 309. For example, the reference sensor elements 504, 505, 506 and the three measuring sensor elements 507, 508 and 509 may be wires. The wires may be formed from the membranes 214 and 215 by using the Bosch edge. The process may also be called releasing the wires.

Figure 6:
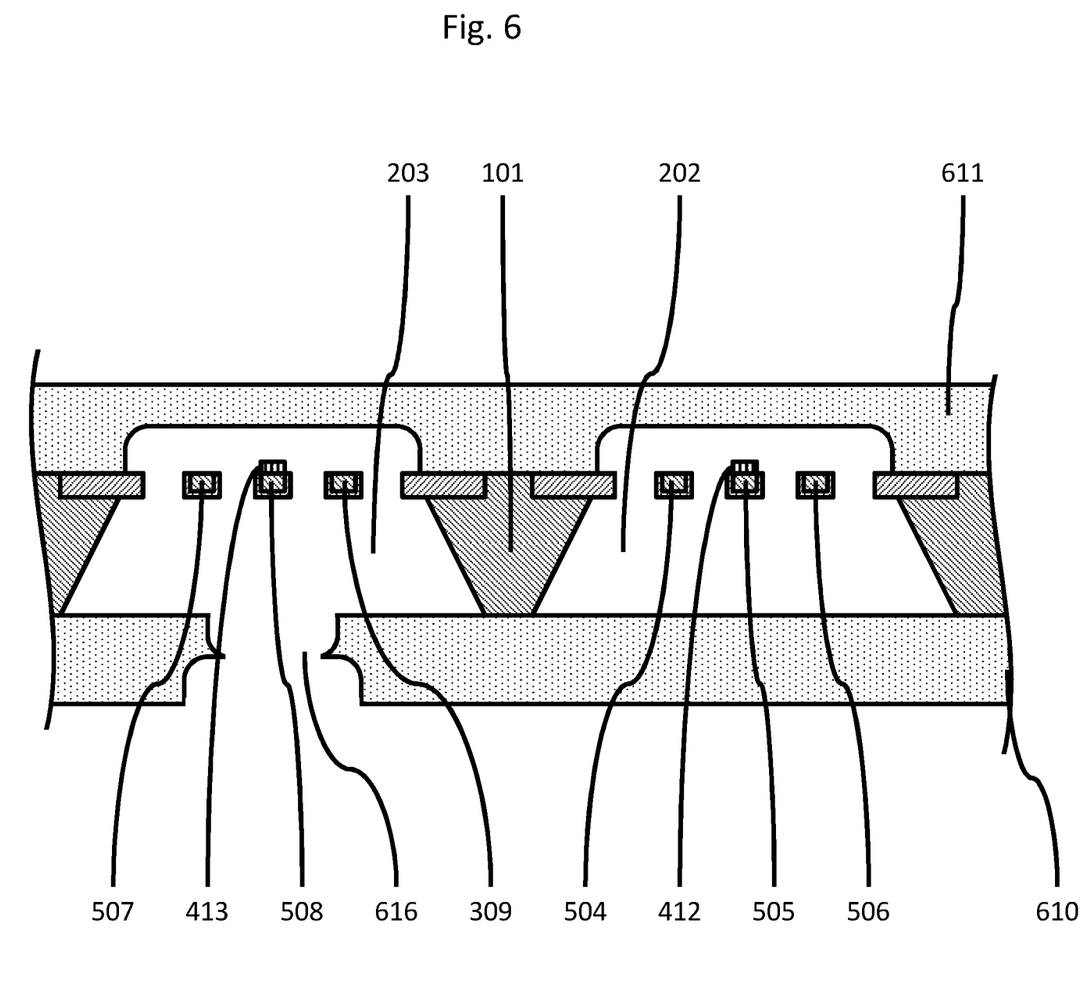
FIG. 6 shows the processed wafer of FIG. 5.

FIG. 6 shows that two covering wafers 610 and 611 are bonded to the semiconductor wafer 101 for sealing, for example, hermetically sealing, the reference cavity 202 and covering the measuring cavity 203. A conduit 616 is provided to allow ambient gas to enter the measuring cavity 203.

Figure 7:
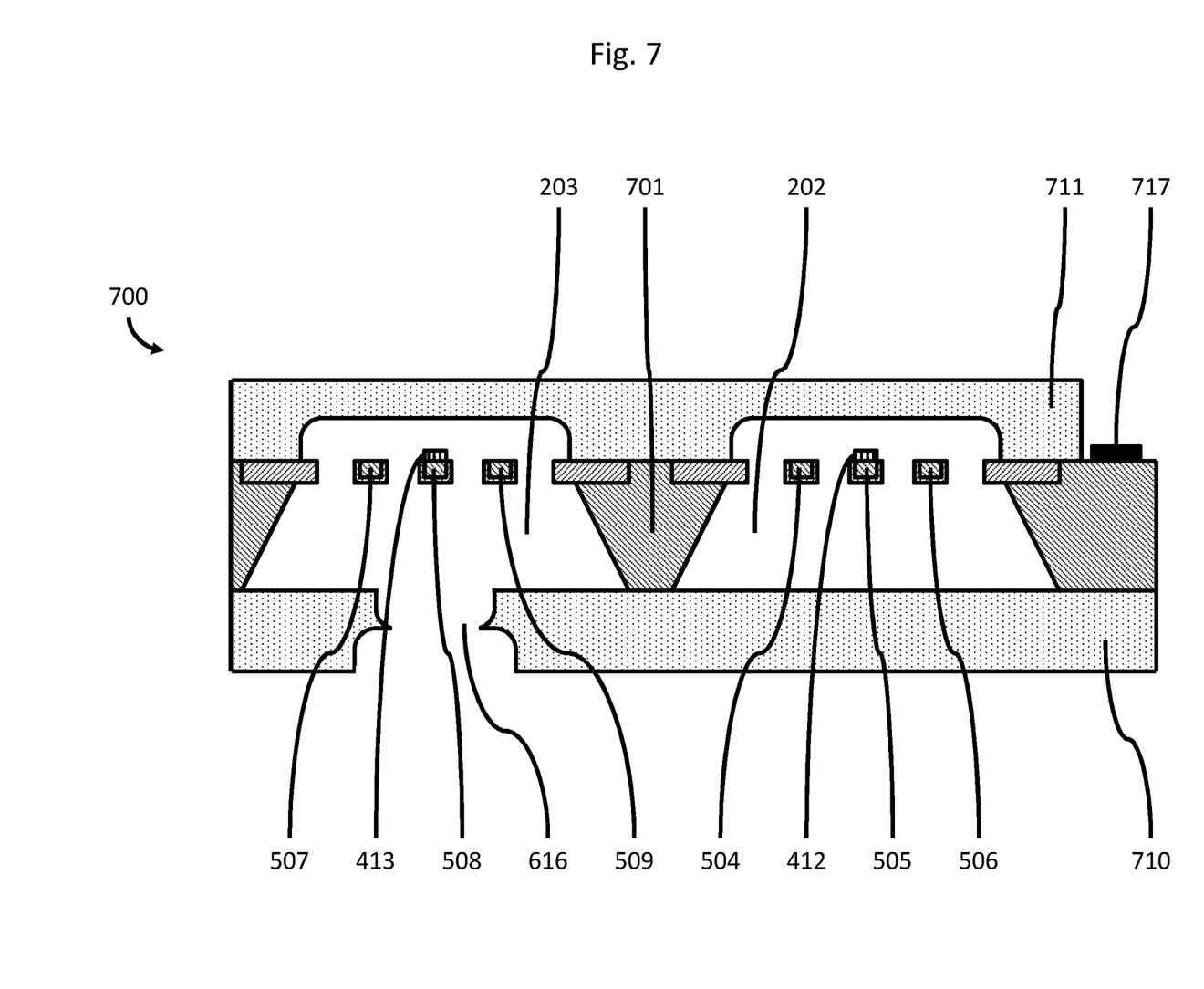
FIG. 7 shows a sensor for measuring a gas property.

In some implementations, the semiconductor wafer 101 with the bonded covering wafers 610 and 611 may be diced to form one or more of the sensors 700 shown in FIG. 7. The one or more sensors 700 may thus be formed using one or more semiconductor manufacturing processes which may render the manufacture of the described sensors very cost effective.

FIG. 7 shows the sensor 700 for measuring a gas property. The sensor 700 may be configured for measuring a gas composition, for example, a hydrogen level. The sensor 700 comprises a semiconductor die 701. A reference cavity 202 and a measuring cavity 203 are provided in the semiconductor die 701. As explained herein before, the reference cavity 202 and the measuring cavity 203 may have been formed by etching. A reference sensor element 504 is arranged in the reference cavity 202 and a corresponding measuring sensor element 507 is arranged in the measuring cavity. As shown in FIG. 7, three reference sensor elements 504, 505, 506 may be provided in the reference cavity 202 and corresponding three measuring sensor elements 507, 508, 509 may be provided in a reference cavity.

The reference cavity 202 is sealed from ambient gas. In some implementations, the reference cavity 202 may be hermetically sealed from ambient gas. In some implementations, the measuring cavity 203 is fluidly connected to ambient gas. In some implementations, a conduit 616 may be provided for fluidly connecting the measuring cavity 203 to ambient gas. The reference sensor elements 504, 505, 506 and/or the measuring sensor elements 507, 508, 509 may be formed as one piece with the semiconductor die 701. Forming the reference sensor elements 504, 505, 506 and/or the measuring sensor elements 507, 508, 509 as one piece with the semiconductor die 701 may facilitate manufacturing of the sensor. Moreover, it may lead to reference sensor elements having the same property as the measuring sensor elements.

Sensors for measuring a gas property, which may also be called gas sensors, may have a cross-sensitivity to different environment characteristics, such as humidity, temperature, flow and concentration of the gas to be sensed. In some cases, dedicated sensors for these additional properties may have to be included in order to differentiate the signal of interest. For example, the complementary temperature sensor may have to be added. This may lead to a complex device, where different dice or sensing elements have to be combined inside the package.

The sensors as disclosed herein may be fabricated with two identical sensing elements (e.g., the reference sensor element and the measuring sensor element) in one die. One element (e.g., the measuring sensor element) is exposed to the ambient of interest and the other element (e.g., the reference sensor element) is enclosed within a hermetically sealed cavity (e.g., the reference cavity). Hence, the package complexity may be reduced. Further, the device sensitivity may be improved.

For example, a differential read out between the two sensor elements (e.g., the reference sensor element and the measuring sensor element) may significantly reduce or even eliminate cross-sensitivity to temperature, as well as other sources of error and operational drift.

The sensor 700 may comprise a covering 710, 711 for sealing the reference cavity 202 and covering the measuring cavity 203. The conduit 616 may be provided in the covering 710 to provide a fluid connection to ambient gas. In some implementations, the covering 710 and/or the covering 711 may be formed from glass. The conduit 616 may be formed by etching the glass covering. In some implementations, the reference cavity 202 may be filled with a gas.

In some implementations, the reference cavity 202 may be filled with inert gas. In some implementations, the reference cavity 202 may be filled with at least one of Nitrogen and Xenon. During manufacturing of the sensor 700, for example, during bonding of the coverings 710, 711 to the semiconductor die 701, a specific gas pressure may be applied, which will be present in the reference cavity 202 afterwards. In some implementations, the gas pressure in the reference cavity may be below 10 mbar. This may be considered as vacuum.

The coverings 710 and 711 may be hermetically bonded to the semiconductor die 710. Thus, no gas may enter the reference cavity 202 or the measuring cavity 203 via the interface of the semiconductor die 701 with the current 711 and 712. Several techniques for hermetically bonding the coverings 710, 711 to the semiconductor die 701 may be used. For example, glass frit may be used for hermetically bonding the coverings 710, 711 to the semiconductor die 701. Other techniques include metal bonding or soldering. In some implementations, an adhesive-free bonding technique may be used for hermetically bonding the coverings 710, 711 to the semiconductor die 701. In some implementations, anodic bonding may be used for bonding the coverings 710, 711 to the semiconductor die 701.

The reference sensor element 504 and the measuring sensor element 507 may have the same structure. In some implementations, the reference sensor element 504 may be formed from the same material as the measuring sensor element 507 and may have the same geometry. In some implementations, the only difference between the reference sensor element 504 and the measuring sensor element 507 may be that one is provided in the reference cavity 202 and the other one in the measuring cavity 203. In some implementations, the reference sensor element 504, the measuring sensor element 507, and the semiconductor die 701 may be formed as one piece.

In some implementations, the reference sensor element 505 may correspond to the measuring sensor element 508 and the reference sensor element 506 may correspond to the measuring element 509.

The semiconductor die 701 may comprise an integrated circuit. The reference sensor element 504 and/or the measuring sensor element 507 may be part of the integrated circuit. In some implementations, components for reading out the reference sensor element 504 and 507 may be directly integrated with the semiconductor die. In some implementations, amplifiers may be provided close to the reference sensor element and the measuring sensor element to avoid noise in the sending signals.

Figure 8:
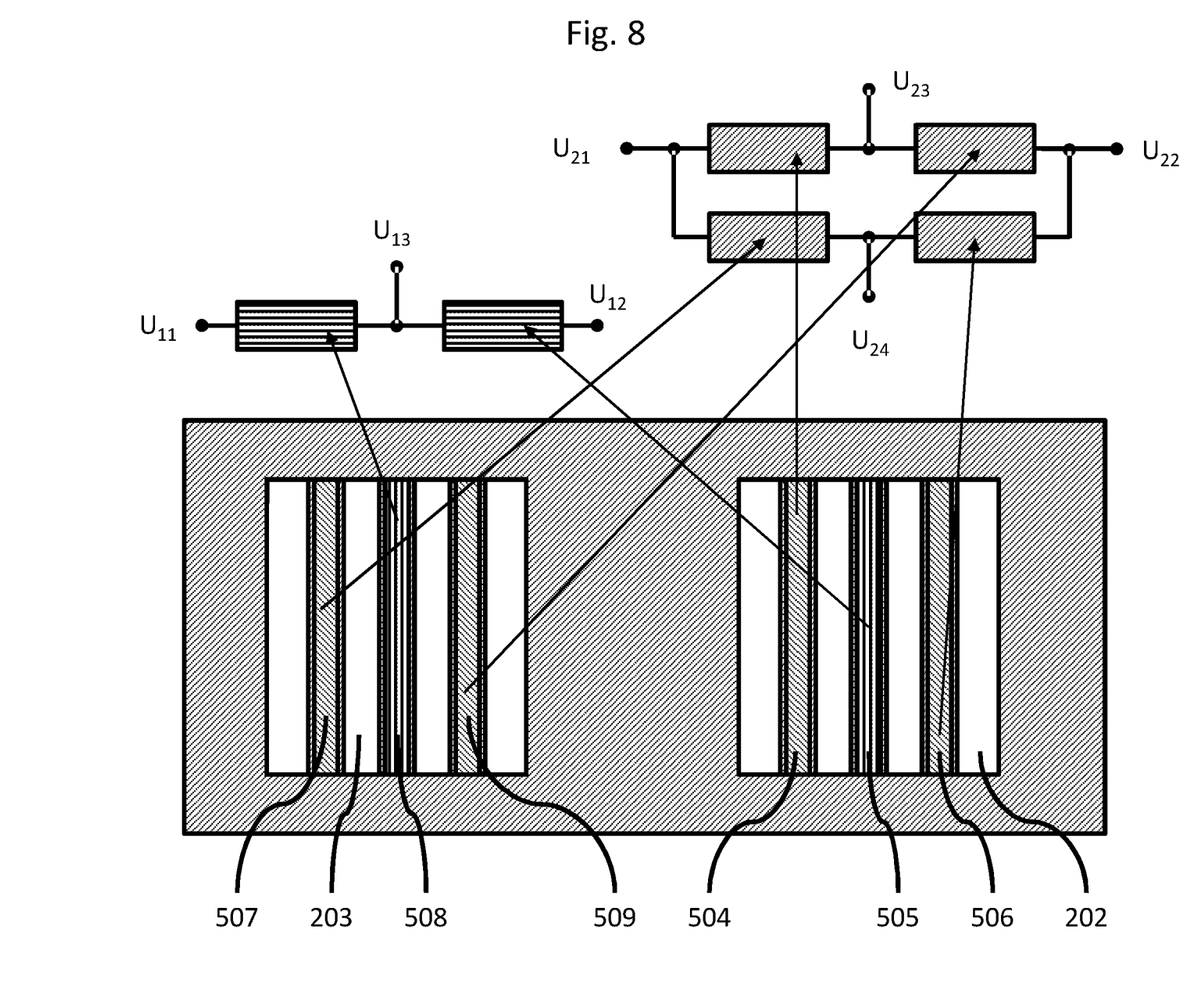
FIG. 8 shows the sensor
Figure 9:
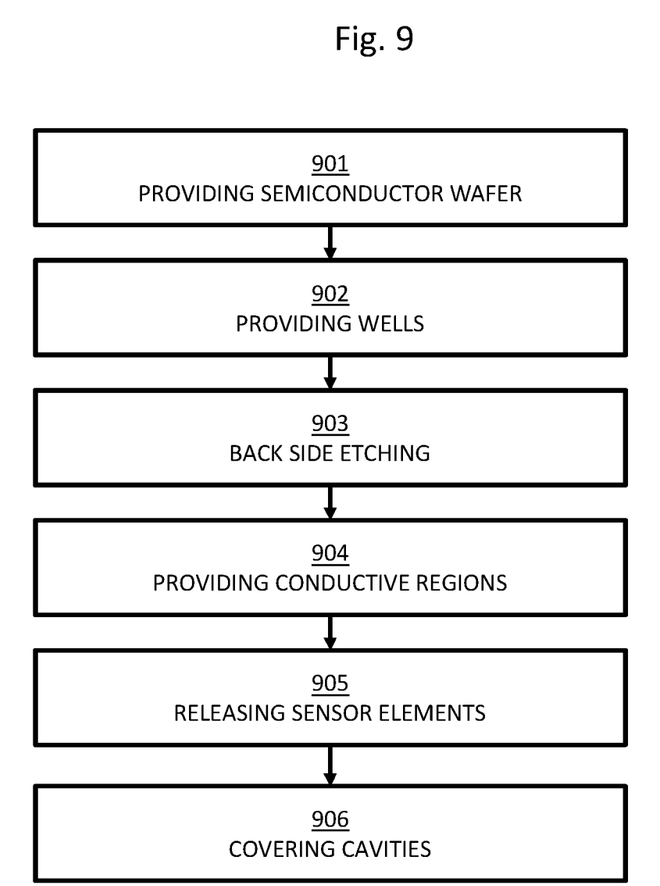
FIG. 9 illustrates a method for manufacturing a sensor.

As shown in FIG. 8, a reference sensor element and a measuring sensor element may be electrically connected to form a half bridge. In some implementations, the reference sensor element 505 and the measuring sensor element 508 may be electrically connected to form half bridge. This may facilitate reading out the sensor.

The sensor 700 may comprise at least two reference sensor elements and at least two measuring sensor elements forming a full bridge. In some implementations, one reference sensor element 504 of the two reference sensor elements 504, 506 may be electrically connected with a first node U23, a first node U23 of one measuring sensor element 509 of the two measuring sensor elements 507, 509 and with a second node U21 to a second node U21 of the other measuring sensor element 507 of the two measuring sensor elements 507 and 509. The other reference sensor element 506 of the two reference sensor elements 504, 506 may be electrically connected with the first node U24 to a first node U24 of the other measuring sensor element 507 of the two measuring sensor elements 507 and 509 and with a second node U22 the second node U22 of the measuring sensor element 504 of the two measuring sensor elements 504 and 506.

Due to the provision of the reference sensor elements in the reference cavity, the sensor 700 may be suitable to be operated between −40° C. and 150° C.

Aspects

In some aspects, the reference sensor element and the measuring sensor element may be formed as corresponding ambulance. Alternatively, as shown in the figures, the reference sensor elements and the measuring sensor elements may be formed as corresponding wires. These may be linear wires or meander wires.

The reference sensor element 505 and the measuring sensor element 508 may comprise a catalytic layer for reacting with gas molecules. In some implementations, the catalytic layer may be formed from platinum and/or palladium for reacting with hydrogen molecules. The catalytic layer may also be formed using additional or different noble gases.

As shown in FIG. 8, the sensor 700 comprises at least two reference sensor elements 504, 505 and at least two measuring sensor elements 507, 508. The reference sensor element 504 corresponds to the measuring sensor element 507. In some implementations, the reference sensor element 505 corresponds to the measuring sensor element 508. The reference sensor element 504 and the measuring sensor element 507 may be configured for using different measurement principle than the reference under element 505 and the second measuring sensor element 508.

For example, the reference sensor element 504 and the measuring sensor element 507 may be configured for measuring a gas concentration via thermal conductivity. For example, the reference sensor element 504 and the measuring sensor element 507 may comprise silicon wires etched on a thin membrane. The silicon wires may be doped to increase the electrical conductance.

In some implementations, the reference sensor element 505 and the measuring sensor element 508 may be configured to measure a gas concentration via catalytic combustion. For example, the catalytic layer may react with gas molecules which may induce a modification of the electrical properties of the reference sensor element 505 and the measuring sensor element 508. By applying a current and heating the respective reference sensor element 505/measuring sensor element 508, the gas molecules may be released again and the sensor may be reset.

According to FIG. 8, a half-bridge electric circuit may be used for the sensor elements which use a catalytic layer technique for detecting a gas concentration and a full-bridge electric circuit may be used for the sensor elements which us a thermal conductivity technique for detecting the gas concentration. This may lead to similar signal levels for both types of sensor elements and facilitate the combination of the measurement results obtained by both techniques.

The combination of two measuring principles within one sensor may further enhance the precision of the sensor. Further gas sensing principles and/or mixture of those sensing principles may be used as well.

The proposed sensor may be particularly useful for automotive powertrains based on hydrogen fuel cells. For example, a sensor of the described type may be located near an exhaust of the fuel cell, in order to control the fuel cell. Heretofore, the sensor may be configured to determine an $H_2$ content of 0 to 40%.

Furthermore, the sensor may be located next to the high pressure $H_2$ tank. The sensor may be configured for sensing an $H_2$ leakage. For this purpose, the sensor may have a sensitivity for a concentration of 0 to 4% $H_2$. In some implementations, the sensor may be located close to a battery pack. The sensor may be configured for detecting out gassing of $H_2$ due to the battery pack being overloaded and/or damaged. For this purpose, the sensor may detect $H_2$ with a concentration of 0 to 4%.

The following aspects are disclosed:

Aspect 1. A sensor for measuring a gas property, a gas composition, and/or a hydrogen level, wherein the sensor comprises a semiconductor die, wherein the semiconductor die comprises a reference cavity and a measuring cavity, wherein a reference sensor element is arranged in the reference cavity, wherein a measuring sensor element is arranged in the measuring cavity, wherein the reference cavity is sealed from ambient gas, wherein the measuring cavity is fluidly connected to ambient gas.

Aspect 2. The sensor of example 1, wherein the reference sensor element and/or the measuring sensor element are formed as one piece with the semiconductor die.

Aspect 3. The sensor of aspect 1 or 2, wherein the sensor comprises a covering, in particular a glass covering, for sealing the reference cavity and covering the measuring cavity.

Aspect 4. The sensor of any one of the preceding aspects, wherein the reference cavity is filled with a gas, such as, for example, an inert gas, such as, for example, at least one of nitrogen and xenon.

Aspect 5. The sensor of any one of the preceding aspects, wherein a gas pressure in the reference cavity is below 10 mbar.

Aspect 6. The sensor of any one of the preceding aspects, wherein the covering is hermetically bonded to the semiconductor die.

Aspect 7. The sensor of any one of the preceding aspects, wherein the reference sensor element and the measuring sensor element have the same structure.

Aspect 8. The sensor of any one of the preceding aspects, wherein the semiconductor die comprises an integrated circuit and wherein the reference sensor element and/or the measuring sensor element are part of the integrated circuit.

Aspect 9. The sensor of any one of the preceding aspects, wherein the reference sensor element and the measuring sensor element are electrically connected to form a half bridge.

Aspect 10. The sensor of any one of the preceding aspects, wherein the sensor comprises at least two reference sensor elements and at least two measuring sensor elements, wherein one of the two reference sensor elements is electrically connected with a first node to a first node of one of the two measuring sensor elements and with a second node to a second node of the other one of the two measuring sensor elements, wherein the other one of the two reference sensor elements is electrically connected with a first node to a first node of the other one of the two measuring sensor elements and with a second node to the second node of the one of the two measuring sensor elements.

Aspect 11. The sensor of any one of the preceding aspects, wherein the sensor is suitable to be operated between −40° C. and 150° C.

Aspect 12. The sensor of any one of the preceding aspects, wherein the reference sensor element and the measuring sensor element are formed as corresponding membranes.

Aspect 13. The sensor of any one of the preceding aspects, wherein the reference sensor element and the measuring sensor element are formed as corresponding wires. In some implementations, the reference sensor element and the measuring sensor element may be formed as corresponding linear wires or meander wires.

Aspect 14. The sensor of any one of the preceding aspects, wherein the reference sensor element and the measuring sensor element comprise a catalytic layer for reacting with gas molecules. In some implementations, the reference sensor element and the measuring sensor element may comprise platinum and/or palladium for reacting with hydrogen molecules.

Aspect 15. The sensor any one of the preceding aspects, wherein the sensor comprises at least two reference sensor elements and at least two measuring sensor elements; wherein a first reference sensor element of the at least two reference sensor elements corresponds to a first measuring sensor element of the at least two measuring sensor elements and a second reference sensor element of the at least two reference sensor elements corresponds to a second measuring sensor element of the at least two measuring sensor elements, and wherein the first reference sensor element and the first measuring sensor element are configured for using a different measurement principle than the second reference sensor element and the second measuring sensor element.

Aspect 16. A method for manufacturing one or more sensors for measuring a gas property, a gas composition, and/or a hydrogen level, wherein the method comprises: providing a semiconductor wafer having a front side and a back side; providing a well with a doping type opposite of a doping type of the semiconductor wafer at the front side of the semiconductor wafer; etching at least one reference cavity and at least one measuring cavity in the back side of the semiconductor wafer to form membranes; providing conductive regions within or at a surface of the membranes, in particular by doping and/or by depositing a conductive material; forming at least one reference sensor element and at least one measuring sensor element from the conductive regions by etching; and bonding, for example, anodic bonding, at least one covering wafer to the semiconductor wafer for sealing the reference cavity and covering the measuring cavity.

Aspect 17. The method for manufacturing one or more sensors for measuring a gas property according to Aspect 14, wherein the method further comprises: depositing a catalytic material on the conductive regions to form a catalytic layer for reacting with gas molecules, such as, for example, depositing platinum and/or palladium for reacting with hydrogen molecules.

Aspect 18. The method for manufacturing one or more sensors for measuring a gas property according to Aspect 15 or 16, wherein the method further comprises: dicing the semiconductor wafer to form the one or more sensors.

While several implementations have been described with reference to the drawing, this description is not intended to be construed in a limited sense. Various modifications and combinations of the illustrative implementations, as well as other implementations, will be apparent to persons skilled in the art upon reference to the description. It is therefore intended that the appended claims encompass any such modifications or implementations.

What is claimed is:

1. A sensor for measuring a gas property, the sensor comprising:
a semiconductor die that defines a reference cavity and a measuring cavity,
wherein the reference cavity is sealed from an ambient gas,
wherein the measuring cavity is fluidly connected to the ambient gas, and
wherein the semiconductor die includes:
a plurality of reference sensor elements arranged in the reference cavity; and
a plurality of measuring sensor elements arranged in the measuring cavity,
wherein the plurality of reference sensor elements and the plurality of measuring sensor elements are conductive regions formed within the semiconductor die,
wherein the plurality of reference sensor elements include a first reference sensor element and one or more second reference sensor elements, and
wherein the plurality of measuring sensor elements include a first measuring sensor element and one or more second measuring sensor elements;
a first catalytic layer arranged on the first reference sensor element and configured to react with gas molecules of a gas to induce a modification of one or more electrical properties of the first reference sensor element; and
a second catalytic layer arranged on the first measuring sensor element and configured to react with the gas molecules of the gas to induce a modification of one or more electrical properties of the first measuring sensor element,
wherein the first reference sensor element and the first measuring sensor element are configured to measure a gas concentration of the gas based on catalytic combustion of the first catalytic layer and the second catalytic layer, respectively,
wherein the one or more second reference sensor elements and the one or more second measuring sensor elements are configured to measure the gas concentration of the gas based on a thermal conductivity of the one or more second reference sensor elements and the one or more second measuring sensor elements being modified by an interaction with the gas molecules of the gas,
wherein the first reference sensor element and the first measuring sensor element are electrically connected to form a half bridge circuit, the half bridge circuit configured to provide a first readout signal representative of the gas concentration of the gas, and
wherein the one or more second reference sensor elements and the one or more second measuring sensor elements are electrically connected to form a bridge circuit, the bridge circuit configured to provide a second readout signal representative of the gas concentration of the gas.

2. The sensor of claim 1, wherein the plurality of reference sensor elements and the plurality of measuring sensor elements are formed as one piece with the semiconductor die.

3. The sensor of claim 1, wherein the reference cavity is filled with a reference gas.

4. The sensor of claim 1, wherein the first reference sensor element and the first measuring sensor element have a same geometric structure.

5. The sensor of claim 1, wherein the semiconductor die comprises an integrated circuit, and
wherein the plurality of reference sensor elements and the plurality of measuring sensor elements are part of the integrated circuit.

6. The sensor of claim 1, wherein the plurality of reference sensor elements and the plurality of measuring sensor elements are formed as corresponding membranes.

7. The sensor of claim 1, wherein the plurality of reference sensor elements and the plurality of measuring sensor elements are formed as corresponding wires.

8. The sensor of claim 1, wherein the first catalytic layer and the second catalytic layer are made of a noble metal.

9. The sensor of claim 1, wherein the plurality of reference sensor elements and the plurality of measuring sensor elements are conductive regions formed from conductive material deposited within the semiconductor die.

10. The sensor of claim 1, wherein the plurality of reference sensor elements and the plurality of measuring sensor elements are conductive regions formed from semiconductor material within the semiconductor die.

11. The sensor of claim 10, wherein the plurality of reference sensor elements and the plurality of measuring sensor elements are formed as one piece with the semiconductor die, and
wherein the plurality of reference sensor elements and the plurality of measuring sensor elements have a first doping type opposite to a second doping type of a body of the semiconductor die.

12. The sensor of claim 1, wherein the plurality of reference sensor elements are formed in a first membrane of the semiconductor die, and
wherein the plurality of measuring sensor elements are formed in a second membrane of the semiconductor die.

13. The sensor of claim 1, wherein the one or more second reference sensor elements include at least two second reference sensor elements,
wherein the one or more second measuring sensor elements include at least two second measuring sensor elements, and
wherein the one or more second reference sensor elements and the one or more second measuring sensor elements are electrically connected to form a full bridge circuit.

14. The sensor of claim 13, wherein a first one of the one or more second reference sensor elements and a first one of the one or more second measuring sensor elements are electrically connected to form a first half bridge circuit of the full bridge circuit, and
wherein a second one of the one or more second reference sensor elements and a second one of the one or more second measuring sensor elements are electrically connected to form a second half bridge circuit of the full bridge circuit.

15. The sensor of claim 1, further comprising:
a first covering wafer bonded to a first surface of the semiconductor die; and
a second covering wafer bonded to a second surface of the semiconductor die opposite to the first surface of the semiconductor die,
wherein the first covering wafer and the second covering wafer enclose the reference cavity, and
wherein the first covering wafer and the second covering wafer partially enclose the measuring cavity.

16. The sensor of claim 15, wherein the plurality of reference sensor elements and the plurality of measuring sensor elements are arranged at the first surface, and
wherein the second covering wafer includes a conduit for providing the ambient gas to the measuring cavity.

17. The sensor of claim 1, wherein the first reference sensor element is encapsulated such that the first reference sensor element is not directly exposed to the reference cavity, the first reference sensor element being at least partially encapsulated by the first catalytic layer,
wherein the first measuring sensor element is encapsulated such that the first measuring sensor element is not directly exposed to the measuring cavity, the first measuring sensor element being at least partially encapsulated by the second catalytic layer,
wherein the one or more second reference sensor elements are directly exposed to the reference cavity, and
wherein the one or more second measuring sensor elements are directly exposed to the measuring cavity for direct exposure to the ambient gas.

18. A sensor for measuring a gas property, the sensor comprising:
a semiconductor die that defines a reference cavity and a measuring cavity,
wherein the reference cavity is sealed from an ambient gas,
wherein the measuring cavity is fluidly connected to the ambient gas,
wherein the semiconductor die includes:
a plurality of reference sensor elements arranged in the reference cavity; and
a plurality of measuring sensor elements arranged in the measuring cavity,
wherein the plurality of reference sensor elements and the plurality of measuring sensor elements are conductive regions formed from semiconductor material within the semiconductor die,
wherein the plurality of reference sensor elements include a first reference sensor element and one or more second reference sensor elements,
wherein the plurality of measuring sensor elements include a first measuring sensor element and one or more second measuring sensor elements,
wherein the first reference sensor element and the first measuring sensor element are configured to utilize catalytic combustion to sense gas molecules of the gas,
wherein the first reference sensor element and the first measuring sensor element have one or more electrical properties that are modified based on the catalytic combustion caused by an interaction with the gas molecules of the gas,
wherein the one or more second reference sensor elements and the one or more second measuring sensor elements are configured to utilize thermal conductivity to sense the gas molecules of the gas,
wherein the one or more second reference sensor elements and the one or more second measuring sensor elements have a thermal conductivity property that is modified based on an interaction with the gas molecules of the gas,
wherein the first reference sensor element and the first measuring sensor element are electrically connected to form a half bridge circuit, the half bridge circuit configured to provide a first readout signal representative of a gas concentration of the gas, and
wherein the one or more second reference sensor elements and the one or more second measuring sensor elements are electrically connected to form a bridge circuit, the bridge circuit configured to provide a second readout signal representative of the gas concentration of the gas.

19. The sensor of claim 18, wherein the sensor is configured to determine the gas concentration of the gas based on the first readout signal and the second readout signal.

20. The sensor of claim 18, wherein the one or more second reference sensor elements include at least two second reference sensor elements, wherein the one or more second measuring sensor elements include at least two second measuring sensor elements, and wherein the one or more second reference sensor elements and the one or more second measuring sensor elements are electrically connected to form a full bridge circuit.

21. The sensor of claim 20, wherein a first one of the one or more second reference sensor elements and a first one of the one or more second measuring sensor elements are electrically connected to form a first half bridge circuit of the full bridge circuit, and wherein a second one of the one or more second reference sensor elements and a second one of the one or more second measuring sensor elements are electrically connected to form a second half bridge circuit of the full bridge circuit.

22. A sensor for measuring a gas property, the sensor comprising:

a semiconductor die that defines a reference cavity and a measuring cavity, wherein the reference cavity is sealed from an ambient gas, wherein the measuring cavity is fluidly connected to the ambient gas, wherein the semiconductor die includes:

a plurality of reference sensor elements arranged in the reference cavity; and a plurality of measuring sensor elements arranged in the measuring cavity, wherein the plurality of reference sensor elements and the plurality of measuring sensor elements are conductive regions formed from semiconductor material within the semiconductor die, wherein the plurality of reference sensor elements include a first reference sensor element and one or more second reference sensor elements, wherein the plurality of measuring sensor elements include a first measuring sensor element and one or more second measuring sensor elements, wherein the first reference sensor element and the first measuring sensor element are configured to utilize catalytic combustion to sense gas molecules of the gas, wherein the one or more second reference sensor elements and the one or more second measuring sensor elements are configured to utilize thermal conductivity to sense the gas molecules of the gas, wherein the first reference sensor element and the first measuring sensor element are electrically connected to form a half bridge circuit, the half bridge circuit configured to provide a first readout signal representative of a gas concentration of the gas, and wherein the one or more second reference sensor elements and the one or more second measuring sensor elements are electrically connected to form a bridge circuit, the bridge circuit configured to provide a second readout signal representative of the gas concentration of the gas.

* * * * *